United States Patent

McCarver et al.

Patent Number: 5,362,306
Date of Patent: Nov. 8, 1994

[54] SURGICAL STOCKINETTE

[75] Inventors: Stacey G. McCarver, Marietta; David C. Strack, Canton; Marsha L. Porter, Roswell; Peter Mathis, Marietta, all of Ga.

[73] Assignee: Kimberly-Clark Corporation, Neenah, Wis.

[21] Appl. No.: 85,332

[22] Filed: Jun. 30, 1993

[51] Int. Cl.⁵ .................. A61F 13/00; A61B 19/08; B32B 3/10
[52] U.S. Cl. ................................ 602/60; 602/63; 128/856; 428/152
[58] Field of Search ............ 602/5, 6, 7, 8, 12, 602/20–22, 41, 44, 45, 46, 61–65; 128/856; 428/152

[56] References Cited

U.S. PATENT DOCUMENTS

| | | | |
|---|---|---|---|
| 2,868,193 | 1/1959 | Kreft | 602/6 |
| 3,232,289 | 2/1966 | Zimmerman | 602/6 |
| 3,934,582 | 1/1976 | Gorrie | 602/62 |
| 3,972,323 | 8/1976 | Boricheski | 602/8 |
| 4,381,611 | 5/1983 | Wishman | 602/45 |
| 4,642,819 | 2/1987 | Ales et al. | 2/400 |
| 4,720,415 | 1/1988 | Vander Wielen et al. | 428/152 |
| 4,770,299 | 9/1988 | Parker | 602/6 |
| 4,770,917 | 9/1988 | Tochacek et al. | 428/95 |
| 4,816,094 | 3/1989 | Pomplun et al. | 156/85 |
| 4,841,958 | 6/1989 | Ersfeld et al. | 128/90 |
| 4,856,502 | 8/1989 | Ersfeld et al. | 128/90 |
| 4,921,743 | 5/1990 | Hansen et al. | 428/102 |
| 4,931,343 | 6/1990 | Becker et al. | 428/95 |
| 4,953,544 | 9/1990 | Hansen et al. | 128/156 |
| 4,957,795 | 9/1990 | Riedel | 602/45 |
| 4,977,011 | 12/1990 | Smith | 602/62 |
| 4,984,584 | 1/1991 | Hansen et al. | 128/898 |
| 5,097,534 | 3/1992 | Viemeister et al. | 2/69 |
| 5,209,801 | 5/1993 | Smith | 602/62 |

Primary Examiner—Michael A. Brown
Attorney, Agent, or Firm—David J. Alexander

[57] ABSTRACT

Disclosed herein is a surgical stockinette for covering and encasing a body extremity such as an armor leg to isolate and protect the extremity during surgery. The stockinette has a generally tubular-shape and is made from a composite material defining a length and a width with the length being longer than the width. The stockinette defines an interior surface and an exterior surface with the tubular-shaped structure defining an open end and a closed end separated by the length. The interior and exterior surfaces are joined circumferentially to one another along substantially the entire length of the tubular-shaped structure. The interior surface is formed from a fibrous material and the overall structure is liquid impervious and circumferentially expandable from a first circumference to a second and larger circumference. Due to the materials and nature of construction, the stockinette of the present invention provides a form-fitting design which is easy to don and remove.

26 Claims, 1 Drawing Sheet

SURGICAL STOCKINETTE

BACKGROUND OF THE INVENTION

The present invention is directed to a surgical stockinette for covering body extremities, especially during surgical procedures. More specifically, the surgical stockinette of the present invention is made from a laminate that has a fibrous body side surface, is liquid impermeable and elastic. The surgical stockinette has low lint characteristics and good comfort and fit.

Many surgical procedures involve the body extremities either because of the surgical procedure being performed directly on the body extremity or the necessity to isolate the body extremity for a particular procedure. Proper sterile technique requires that, absent the specific area being operated upon, the remainder of the patient should be isolated from the surgical site to reduce the risk of contamination and infection. Generally a surgical drape is used to cordon off the surgical site from the remainder of the patient. However, certain procedures require the access to or exposure of the arms and legs which in turn necessitates separate surgical coverings for the exposed limbs. A practice in the past has been to encase the exposed limb in a surgical wrap such as is shown in U.S. Pat. No. 3,934,582. A product similar to this is sold by Johnson and Johnson Medical, Inc. and utilizes a knitted polyester, cotton, or polyester/cotton blend interliner and an elastomeric film outer layer made from Elastoflex ® K film from Clopay Corporation of Cincinnati, Ohio. Elastoflex ® K film is made of Kraton ® polymers from Shell Corporation. Each of the two materials or pieces is separately formed into a tube with one end closed. The knitted tube material is inserted inside the tubular elastic film material, however there is no actual joining of either layers to the other. Thus, the inner and outer layers can twist, bunch-up and move independently of one another.

This type of wrap or legging is rolled into a ring before application. To apply the wrap the closed end of the wrap is placed over the foot or hand of the patient and the remainder of the wrap is then unrolled by rolling the wrap down and over the limb in the direction of the torso of the patient. Such products are bulky and loose fitting. The knitted inner layer also tends to move and shift relative to the outer layer of elastic rubber thereby making the positioning of the wrap unstable during use.

If the surgical procedure is to be performed on the wrapped limb, an incision is often made directly through both the inner and outer layers of the wrap in the area directly surrounding the incision. Here again because the inner and outer layers are not attached to one another, cleanly cutting through both the layers can sometimes be difficult, especially if the knitted material is bunched-up underneath the elastic rubber outer layer. Furthermore, the knitted material when cut tends to unravel thereby producing a large amount of lint which can enter the wound or incision site thereby causing complications.

It is therefore an object of the present invention to provide a surgical stockinette which is compact, form-fitting and low linting. It is another object of the present invention to provide a surgical stockinette where the inner layer will not move independent of the outer layer. It is yet a further object of the present invention to provide a surgical stockinette which can be easily cut to expose the surgery site.

Another problem with existing surgical wraps is the lack of conformability to the extremity being wrapped. It is therefore yet another object of the present invention to provide a surgical stockinette with improved fit and comfort.

These and other objects of the present invention will become more apparent upon a further review of the following specification, drawings and claims.

SUMMARY OF THE INVENTION

The present invention is directed to a surgical stockinette for covering and protecting body extremities including the arms and legs during a surgical procedure. The stockinette has a generally tubular-shape and is made from a composite material defining a length and a width with the length being longer than the width. The stockinette defines an interior surface and an exterior surface with the tubular-shaped structure defining an open end and a closed end separated by the length. The interior and exterior surfaces are joined circumferentially to one another along substantially the entire length of the tubular-shaped structure. The interior surface is formed from a fibrous material and the overall structure is liquid impervious and circumferentially expandable from a first circumference to a second and larger circumference. In a more refined embodiment, the stockinette is made from a composite material including an inner layer made from a fibrous nonwoven web and an outer layer made from a liquid impervious film. Disposed between and bonded to the inner and outer layers is an elastic layer which is bonded or joined to the inner and outer layers by adhesive, heat bonding, ultrasonic bonding, or other suitable means. The elastic layer is secured between the inner and outer layers while the elastic layer is in an expanded state. Once the bonding of the materials has been completed, the material is allowed to relax and contract. Portions of the material can then be cut and formed into the generally tubular-shape. As a result, the stockinette can be expanded from a first circumference to a second and larger circumference during the donning and/or wearing of the stockinette. Generally both the fibrous nonwoven web and the liquid impervious film will be nonelastic though elastic materials are not outside the scope of the present invention. To ensure good fit the stockinette must be capable of expanding at least about its circumference. Typically, the composite material will be able to stretch or expand at least 200% or three times its per unit width. Depending on the type of elastic layer being used, the stockinette may be stretchable or expandable in several directions. To provide increased comfort and fit, the stockinette can be tapered from its open end to its closed end such that the diameter of the stockinette at its open end is greater than the diameter of the stockinette at its closed end.

Once the stockinette has been formed, the inner surface comprising the fibrous nonwoven material provides a soft, low linting surface adjacent the wearer's skin. In addition, because the components of the stockinette are laminated together, they form a very thin and compact material. Lastly, because the inner and outer layers are directly attached to one another, via the elastic layer, there is no shifting between the inner and outer layers. As a result, it is easy to cut through the material forming the stockinette of the present invention.

DETAILED DESCRIPTION OF THE INVENTION

Figure 1:
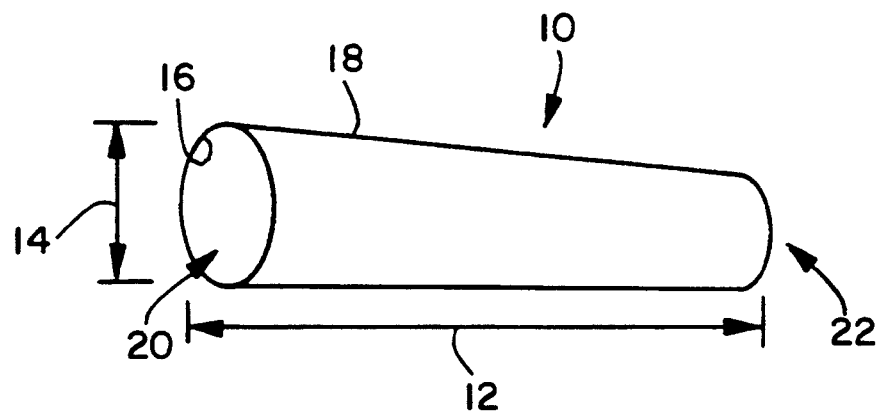
FIG. 1 is a schematic side view of a surgical stockinette according to the present invention.

The present invention is directed to a compact and form fitting surgical stockinette for covering, isolating and protecting body limbs such as the arms and legs. Referring to FIG. 1, in the broadest sense the present invention relates to a generally tubular-shaped structure 10 defining a length 12 and a width 14 with an interior surface 16 and an exterior surface 18. The tubular-shaped structure 10 defines an open end 20 and a closed end 22 separated by said length 12. Due to the nature of the materials forming the tubular-shaped structure 10, the interior surface 16 and exterior surface 18 are joined circumferentially to one another along substantially the entire length of the tubular-shaped structure 10. By joined it is meant that there is some degree of physical attachment of the interior and exterior surfaces through the thickness of the structure 10. Thus two separate layers of material simply resting on top of or positioned adjacent to one another without further connection would not be considered joined to one another. If two or more separate layers are used to form the structure 10, they would be deemed joined to one another along substantially the entire length if they were joined along at least 80% of the length at some point or points about the circumference of the structure. Typically if two or more layers are used, they can be joined to one another by such methods as, for example, laminating, gluing, thermal and ultrasonic bonding, stitching and hydraulically needling (collectively "joining"). Gluing can be achieved, for example, through the use of hot melt and solvent based adhesives. Bonding of separate layers can be achieved, for example, through the use of heat and/or pressure such as with ultrasonic bonding equipment and heated pattern rolls or smooth rolls.

To provide a sufficient degree of comfort and, if desired, absorbency, the interior surface 16 of the structure 10 should be formed from a fibrous material. Examples of fibrous materials include, but are not limited to, woven materials, knitted materials, nonwoven materials and flocked materials. Examples of nonwoven materials include, but are not limited to, spunbond webs, meltblown webs, bonded carded webs, solution spun webs, air-laid webs and wet-laid webs.

The fibers themselves which form the fibrous material can range from relatively short staple length fibers to more continuous fibers such as are found in knitted, woven, spunbond and meltblown materials. Fiber diameters will typically range from about 2 to about 25 microns though fiber sizes outside this range may also be used for specific end-use applications.

The fibers can be made from a variety of natural and synthetic materials including, but not limited to, cotton, rayon, polyolefins, polyamides, copolymers of the foregoing and generally any polymer or resin which can be drawn, extruded or otherwise formed into fibers.

The overall structure should be liquid impervious so that the stockinette will not readily pass such liquids as water, blood, body fluids and irrigation liquids. Thus, by liquid impervious it is meant that a sample of the overall material can withstand penetration of a 100 centimeter column of water pursuant to Test Method 5514, Federal Test Methods No. 191A.

Given the fact that the interior surface should be fibrous, making the stockinette liquid impervious will most likely require adding another component to the stockinette such as a film or liquid impervious coating. Liquid impervious coatings can be achieved through well known techniques such as extrusion coating processes which can be used to apply elastic or non-elastic materials directly to the fibrous interior surface 16 to form a liquid impervious exterior surface 18. Suitable extrusion coating materials include, but are not limited to, polyolefins, polyesters and copolyesters, ethylene copolymers and polyurethanes. In addition to extrusion coated fibers or coatings, the stockinette can be made liquid impervious through the use of pre-formed films which are then joined to the fibrous component by such techniques as thermal bonding, ultrasonic bonding and gluing with hot melt and solvent based adhesives.

The stockinette according to the present invention should be expandable and, if desired, elastic. By "expandable" it is meant that the stockinette 10 is capable of being stretched from a first circumference to a second and larger circumference so that the stockinette can be placed over a body limb and be relatively form fitting. Currently available products do not do this due to the high stretching forces required to expand their circumferences. By "elastic" it is meant that once the stockinette has been expanded to its second circumference and the expanding forces are released, the circumference of the stockinette will retract or recover to a circumference less than the second circumference and more particularly to a circumference which is within 95 percent of the original circumference. To accomplish this, at least one component of the stockinette must be elastic, i.e., capable of being stretched from a first length to a second length and then, upon release of the stretching forces, retracting or recovering to a second length which is within 95 percent of the first or original length.

Many polymers, fibers and materials today are elastic. As a result, it is possible to make elastic woven materials, elastic knit materials, elastic nonwoven materials and elastic films. These elastic materials, once formed, can be stretched and then, while held in a stretched state, be joined to one or more other materials or layers of the stockinette and then be allowed to retract thereby gathering up or puckering the other layers and forming a stretchable and or elastic composite which can then be formed into a stockinette. An example of a process for forming such a composite can be found in U.S. Pat. No. 4,720,415 to Taylor et al. which is commonly assigned to the assignee of record and incorporated herein by reference in its entirety.

Figure 2:
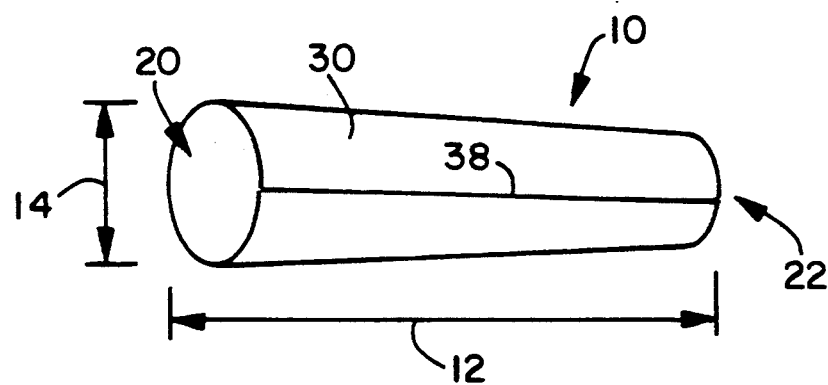
FIG. 2 is a schematic side view of a surgical stockinette according to the present invention.
Figure 3:
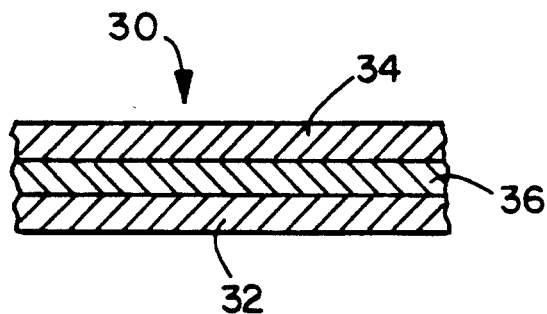
FIG. 3 is a cross-sectional side view of the material forming the stockinette of FIG. 2.

A more refined embodiment of a stockinette 10 according to the present invention is shown in FIGS. 2 and 3. The stockinette 10 in FIG. 2 is a generally tubular-shaped, three layer composite material 30. The material 30 includes an inner layer 32 made from a fibrous nonwoven web and an outer layer 34 made from a liquid impervious film. Disposed between and attached to the inner and outer layers 32 and 34 respectively is an elastic layer 36 which is capable of being expanded in at least one direction and preferably circumferentially about the stockinette in a direction parallel to the width and perpendicular to the length so that the stockinette 10 can be expanded from a first relaxed circumference to a second and larger circumference.

As shown in FIG. 2, the stockinette 10 can be tapered in shape with the open end 20 having a larger diameter than the closed end 22. This is to facilitate the conformity of the stockinette to the generally tapering dimensions of both the arm and the leg of the human body. Generally the open end 20 will have a diameter ranging from between about four and about twelve inches and the closed end 22 will have a diameter ranging between about three and about eight inches. The length 12 of the stockinette 10 is also variable but generally will range between about eighteen and about forty-eight inches. It should be noted, however, that dimensions outside those described are also considered to be within the scope of the present invention.

The interior layer 32 will most typically have a basis weight ranging from about 0.4 ounces per square yard to about 3 ounces per square yard. The fibers used to make the nonwoven will range in size from about 2 microns to about 25 microns in diameter. When utilizing a laminate such as a spunbond/meltblown/spunbond composite, a typical basis weight per layer will be about 0.20 to about 0.45 ounces per square yard for the meltblown layer and about 0.30 to about 0.75 ounces per square yard for each of the spunbond layers.

The outer layer 34 is made from a liquid impervious film. For health care applications, it is desirable that the outer layer 34 be liquid-impervious to protect the patient and assist in maintaining the sterile field. The film thickness will range from about 0.5 mil to about 3 mils. Suitable film materials include polyolefins, ethylene copolymers, copolyesters and polyurethanes. A particularly suitable polymer film is referred to as a Catalloy ® polymer film which utilizes Himont Catalloy ® polymer from Himont U.S.A. of Wilmington, Del.

The means for applying tension to the stockinette 10 in FIG. 2 is an elastic layer 36 positioned between the inner layer 32 and the outer layer 34. The elastic layer 36 may be made from any number of materials, including, but not limited to, Kraton ® polymer, Urethane polymer, Estane ® polymer and Pebax ® polymer. The purpose of the elastic layer 36 is to impart the elasticity to the stockinette for fit and conformity to the particular appendage being covered. The elastic layer 36 should have good stretch recovery so that the stockinette 10 can be expanded and then retracted to approximately the same circumference prior to stretching. It is not desirable that the material permanently deform as this will create an improper fit and detract from the appearance and functionality of the device.

To form the stockinette 10 from the composite materials, lamination, bonding, or some other means of joining the layers is necessary. To this end, it has been found particularly useful to use in combination a Kraton ® polymer meltblown web as described above as the elastic layer 36, a polypropylene spunbonded web as the inner layer 32, and a Catalloy ® polymer film as the outer layer 34. This is because, with this configuration, all three layers are polyolefin based and therefore compatible for ultrasonic bonding. Thermo-mechanical bonding through the use of heated calender rolls is another means for laminating the materials together. Alternatively, the materials may be bonded together using an adhesive. Suitable adhesives include hot melt adhesives, solvent-based adhesives, and powdered adhesives.

When using adhesives, it has been found that application rates in the range of 0.15 to 0.45 ounces per square yard (5 to 15 grams per square meter) of adhesive is adequate to bond the various layers together. One such adhesive suitable for use with the present invention is Findley spray melt adhesive 2096 from Findley Adhesives, Inc. from Wauwatosa, Wis.

To form the material 30 for the stockinette 10 of the present invention, a roll of elastic fibrous nonwoven material 36 is unwound or formed under tension so as to place the elastic fibrous material in an elongated state. Next, a roll of non-elastic nonwoven fibrous web 32 is unwound adjacent to one face of the elongated elastic material 36. A roll of liquid impervious film 34 is unwound adjacent to the opposite face of the nonwoven elastic member. The three layers are then thermally or ultrasonically point bonded over substantially the entire surface while the composite is still held under tension. Generally, the overall bond area will be from about 10 to about 30 percent. Following lamination, the composite is allowed to relax to its pre-stretched state before being wound onto a roll or subsequently converted. After the material 30 has been formed, it can be cut into predetermined lengths, formed into a generally tubular-shape and then seamed by stitching, gluing, ultrasonically bonding or other means to form a seam 38 such as is shown in FIG. 2. Note that the material should be cut and formed into a tube such that the stretch in the composite material 30 runs circumferentially about the tube. Next, one end 22 of the tube can be sealed as by any one of the means used for forming the seam 38 thereby creating the closed end 22.

An example of such a stockinette 10 according to the present invention was made by first creating an inner layer of nonwoven material. The inner nonwoven layer 32 was a 0.4 ounce per square yard spunbond nonwoven web made from polypropylene fibers ranging in size from about 18 to about 25 microns.

The outer layer 34 of the surgical stockinette according to the present invention was non-elastic and made from a 0.6 mil Catalloy ® polymer film made by Edison Plastics of South Plainfield, N.J.

Sandwiched between the non-elastic inner and outer layers was a meltblown middle layer 36 with a basis weight of 3.6 ounces per square yard made of Kraton ® polymer, with fiber sizes ranging from 5 to 15 microns in diameter. The middle, elastic layer was elongated 300% and the three layers were bonded together using heat and pressure to form an elastic composite having an overall basis weight of 4.6 ounces per square yard.

Once the stockinette material was bonded it was allowed to relax thereby gathering up and puckering the inner and outer layers 32 and 34 as the elastic middle layer 36 retracted back toward its original length. The material was then cut into a length of approximately forty-eight inches with a width of approximately fourteen inches and joined along its length by a thermal impulse sealed seam 38 to form a tube with the stretch of the laminate material running circumferentially about the tube. One end of the tube was also sealed off by a thermal impulse sealed seam to form a closed end 22 which was opposed to the open end 20 thereby forming a stockinette 10 according to the present invention. During normal production runs, once the stockinette was formed, it would be rolled into a ring or donut, packaged and then sterilized for subsequent use.

To don the stockinette, the rolled open end 20 is placed over the desired appendage such as the foot or hand and the closed end 22 is brought into close proximity or contact with the particular appendage. Next the rolled portion is unrolled down over the appendage until the desired portion of the appendage has been covered. If desired, the material of the stockinette can be cut away in the area of the incision site. Due to the nature of the materials and the bonding between the layers, very little lint is created as compared to previous executions which use knitted materials which tend to unravel and release big pieces of lint once they are cut.

A particular advantage of the stockinette of the present invention is its form fitting nature and ease of donning. The force required to stretch a stockinette material will affect the ability to put the stockinette on a patient's limb. This is primarily because of the tension or stretch force of the material used to make the stockinette. Stockinette materials which require a large amount of force to be stretched in turn create stockinettes which require a large amount of force to effect donning which can in turn create situations which lead to contamination of the stockinette.

When applying a stockinette to a patient's limb, the hospital must do so in a sterile manner. To this end, the stockinette comes supplied in a rolled up form much like a donut which is placed over the patient's limb and then unrolled up the patient's limb to complete the application process. If the tension in the stockinette material is too high, it is not uncommon for the hospital attendant's hands to slip off the donut portion of the stockinette and contact the skin of the patient thereby contaminating the worker and patient and necessitating the removal of the contaminated stockinette and the application of a new sterile stockinette. To overcome this problem, stockinettes commonly available today are made very loose and baggy because of the high stretch forces of the materials. An example of such a stockinette is the Johnson & Johnson Barrier ® Sterile Impervious Stockinet code 0274 from Johnson & Johnson Medical, Inc. of Arlington, Tex. This stockinette is very baggy and loose and, as shown below, takes a large amount of force to stretch the stockinette to a diameter larger than its unstretched diameter. This stockinette also has a relative constant diameter across its entire length. As a result, the closed end usually has a diameter and circumference which is much larger than, for example, the hand of the patient. Thus the fit over the hand is very loose.

To compare the amount of force required to stretch the material of the present invention versus that of the above-described Johnson & Johnson product, a series of tests were performed to compare the stretch forces needed to expand the material from the stockinette manufactured and sold by Johnson & Johnson Medical Company and that of the present invention.

The Johnson & Johnson stockinette consists of two separate tubes of material with one tube being nested within but unattached to the other tube. The inner tube is a knit material with a closed end and an open end while the exterior tube is a layer of KRATON ® material which is rubber-like and somewhat elastic. The stockinette according to the present invention comprised the three layer structure described above. Five samples of the two stockinettes were cut from their respective specimens in the form of 3"×6" strips. Lines were drawn across the widths of the samples at a distance of 1" from both the top and bottom of each of the samples. The samples were placed lengthwise within the jaws of a Sintech tensile tester such that the initial jaw separation or gap was 4". The samples were expanded at a crosshead speed of 12 inches per minute until a predetermined percent of stretch was reached at which point the samples were held under tension for one minute. The peak load in pounds required to stretch the sample to the desired length was then recorded in pounds. After one minute the tension was released and the samples were removed from the jaws. After removal of the samples from the jaws of the tensile tester the samples were allowed to rest for one minute and the length of the material between the two lines (originally 4") was measured and recorded. Based upon these measurements, the percent recovery was calculated using the following formula:

$$\% \text{ Recovery} = \left\{ 1 - \left[ \frac{\text{recovered length} - \text{original length}}{\text{stretched length}} \right] \right\} \times 100$$

The average load and percent recovery for the five sample replications were calculated at 50, 100, 200 and 300 percent stretch for the specimens of the present invention and the J&J stockinette. This represented measurements at stretched lengths of 6, 8, 12 and 16 inches. The results are set forth in Table I below.

TABLE I

| % Strength | Stretched Length | Stockinette of the Present Invention | | Johnson and Johnson Stockinette | | |
|---|---|---|---|---|---|---|
| | | Average Peak Load (lbs) | % Recovery | Average Peak Load (lbs) | % Recovery Film | Knit |
| 50 | 6" | 1.05 | 100.0 | 2.94 | 100.0 | — |
| 100 | 8" | 1.29 | 98.0 | 3.80 | 97.5 | — |
| 200 | 12" | 2.95 | 97.7 | 5.99 | 96.7 | 93.5 |
| 300 | 16" | 9.70 | 97.0 | 19.18 | 95.5 | 81.5 |

As can be seen from Table I, to expand the sample piece of stockinette material of the present invention from its original four inch length to six inches (50 percent stretch) required roughly one third the force required to stretch the Johnson and Johnson stockinette. At 100 percent stretch the Johnson and Johnson stockinette again required almost three times the stretching force and at 200 and 300 percent approximately twice the force required to expand the stockinette of the present invention to the same level. Thus at all levels of stretching tested, the stockinette of the present invention is much easier to expand.

The results from Table I also show that the stockinette of the present invention is also capable of providing better fit. At all levels of stretch the stockinette of the present invention exhibited better recovery than the competitor stockinette. In addition, at elevated levels of stretching (200 and 300 percent) it was observed that when the tensile tester tension was released, the knit portion of the competitor samples was sagging thus indicating a lower level of recovery. At 300 percent stretch, the knit portion of the competitor samples recovered only 81.5 percent of its original length. This coupled with the unattached nature of the knit and Kraton ® tubes increases the risk of poor fit after donning. This in turn can make incisions through the two layers more difficult and give rise to shifting of the stockinette on the patient's limb which is also undesirable. In contrast, the stockinette of the present invention provided high levels of stretch recovery (in excess of 97 percent) even at high stretch levels (300 percent).

Having thus described the invention in detail it should be understood that various modifications and changes can be made to the present invention without departing from the spirit and scope of the following claims.

We claim:

1. An expandable, liquid impervious surgical stockinette having a length, the stockinette comprising:
   an exterior layer; and
   a fibrous interior layer joined circumferentially to the exterior layer substantially along the entire length of the stockinette; and
   wherein the stockinette, when stretched about 300 percent, has an average peak load of less than 10 pounds.

2. The stockinette of claim 1, having, when stretched 200 percent, an average peak load of less than 3 pounds.

3. The stockinette of claim 2, having, when stretched about 100 percent, an average peak load of less than 2 pounds.

4. The stockinette of claim 3, having, when stretched about 50 percent, an average peak load of less than 1.5 pounds.

5. The stockinette of claim 1, wherein the fibrous interior layer is formed from a material selected from the group consisting of woven materials, knitted materials, nonwoven materials, and flocked materials.

6. The stockinette of claim 5, wherein the nonwoven material is selected from the group consisting of spunbond webs, meltblown webs, bonded carded webs, solution spun webs, air-laid webs and wet-laid webs.

7. The stockinette of claim 1, wherein the exterior layer is a liquid impervious film.

8. The stockinette of claim 1, wherein the exterior layer is a liquid impervious coating.

9. The elastic, liquid impervious surgical stockinette having a length, the stockinette comprising:
   an exterior layer; and
   a fibrous interior layer joined circumferentially to the exterior layer substantially along the entire length of the stockinette; and
   wherein the stockinette, when stretched about 300 percent, has an average peak load of less than 10 pounds and a recovery of at least about 97 percent.

10. The stockinette of claim 9, having when stretched about 200 percent, an average peak load of less than 3 pounds.

11. The stockinette of claim 10, having when stretched about 100 percent, an average peak load of less than 2 pounds.

12. The stockinette of claim 11, having when stretched about 50 percent, an average peak load of less than 1.5 pounds.

13. The stockinette of claim 9, wherein the fibrous interior layer is formed from a material selected from the group consisting of woven materials, knitted materials, nonwoven materials and flocked materials.

14. The stockinette of claim 13, wherein the nonwoven material is selected from the group consisting of spunbond webs, meltblown webs, bonded carded webs, solution spun webs, air-laid webs and wet-laid webs.

15. The stockinette of claim 9, wherein the exterior layer is a liquid impervious film.

16. The stockinette of claim 9, wherein the exterior layer is a liquid impervious coating.

17. A elastic, liquid impervious surgical stockinette having a length, the stockinette comprising:
   an exterior layer;
   a fibrous interior layer;
   an elastic layer disposed between the exterior and interior layers, the elastic layer being joined circumferentially to the exterior and interior layers substantially along the entire length of the stockinette; and
   wherein the stockinette, when stretched about 300 percent, has an average peak load of less than 10 pounds and a recovery of at least about 97 percent.

18. The stockinette of claim 17, having, when stretched about 200 percent, an average peak load of less than 3 pounds.

19. The stockinette of claim 18, having, when stretched about 100 percent, an average peak load of less than 2 pounds.

20. The stockinette of claim 19, having, when stretched about 50 percent, an average peak load of less than 1.5 pounds.

21. The stockinette of claim 17, wherein the fibrous interior layer is formed from a material selected form the group consisting of woven materials, knitted materials, nonwoven materials and flocked materials.

22. The stockinette of claim 21, wherein the nonwoven material is selected from the group consisting of spunbond webs, meltblown webs, bonded carded webs, solution spun webs, air-laid webs and wet-laid webs.

23. The stockinette of claim 17, wherein the exterior layer is a liquid impervious film.

24. The stockinette of claim 17, wherein the exterior layer is a liquid impervious coating.

25. The stockinette of claim 17, wherein the exterior layer is puckered when the stockinette is in a relaxed state.

26. A tapered, elastic, liquid impervious surgical stockinette having a length, the stockinette comprising:
   a puckered exterior liquid impervious film layer;
   a fibrous nonwoven spunbonded polypropylene web interior layer;
   an elastic layer disposed between the exterior and interior layers, the elastic layer being joined circumferentially to the exterior and interior layers substantially along the entire length of the stockinette; and
   wherein the stockinette, when stretched about 50 percent, has an average peak load of less than 1.5 pounds and a recovery of at least about 97 percent.

* * * * *

UNITED STATES PATENT AND TRADEMARK OFFICE
CERTIFICATE OF CORRECTION

PATENT NO. : 5,362,306

DATED : November 8, 1994

INVENTOR(S) : S. G. McCarver, D. C. Strack, M. L. Porter, M. P. Mathis

It is certified that error appears in the above-identified patent and that said Letters Patent is hereby corrected as shown below:

```
Column 3, lines 42--43, "and-/or" should read --and/or--;
Column 9, line 41, "materials, and" should read --materials and--;
Column 9, line 50, "The elastic" should read --An elastic--;
Column 9, line 60, "having" should read --having,--;
Column 9, line 63, "having" should read --having,--;
Column 10, line 1, "having" should read --having,--;
Column 10, line 38, "selected form" should read --selected from--;
In the Abstract, line 2, "armor" should read --arm or--.
```

Signed and Sealed this

Twenty-third Day of January, 1996

Attest:

BRUCE LEHMAN

Attesting Officer

Commissioner of Patents and Trademarks